US012751654B2

(12) United States Patent
VandenBrink et al.

(10) Patent No.: US 12,751,654 B2
(45) Date of Patent: Oct. 6, 2026

(54) BLOOD DRAW DEVICE WITH ANTI-BUCKLING FEATURE

(71) Applicant: Becton, Dickinson and Company, Franklin Lakes, NJ (US)

(72) Inventors: Evan Barbour VandenBrink, San Mateo, CA (US); Weston F. Harding, Lehi, UT (US); Curtis H. Blanchard, Herriman, UT (US); Megan S. Scherich, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 640 days.

(21) Appl. No.: 18/196,666

(22) Filed: May 12, 2023

(65) Prior Publication Data

US 2023/0363676 A1 Nov. 16, 2023

Related U.S. Application Data

(60) Provisional application No. 63/342,366, filed on May 16, 2022.

(51) Int. Cl.
*A61B 5/15* (2006.01)
*A61B 5/151* (2006.01)

(52) U.S. Cl.
CPC ...... *A61B 5/150992* (2013.01); *A61B 5/1513* (2013.01)

(58) Field of Classification Search
CPC ............ A61B 5/150992; A61B 5/1513; A61B 5/150389; A61B 5/150404; A61B 5/150519; A61B 5/153
See application file for complete search history.

(56) References Cited

U.S. PATENT DOCUMENTS

| | | | | |
|---|---|---|---|---|
| 11,090,461 | B2 * | 8/2021 | Ehrenreich | A61B 5/150992 |
| 2018/0022880 | A1 | 1/2018 | Takahashi et al. | |
| 2018/0028800 | A1 | 2/2018 | Devgon et al. | |
| 2018/0272107 | A1 * | 9/2018 | Ehrenreich | A61B 5/150748 |
| 2020/0100716 | A1 | 4/2020 | Devgon et al. | |
| 2021/0022655 | A1 | 1/2021 | Devgon et al. | |

FOREIGN PATENT DOCUMENTS

| | | | |
|---|---|---|---|
| AU | 2015306728 | A1 | 2/2017 |
| CA | 3013460 | A1 | 8/2017 |
| WO | WO2021194761 | A1 | 9/2021 |

* cited by examiner

*Primary Examiner* — May A Abouelela
*Assistant Examiner* — Yasmeen S Warsi
(74) *Attorney, Agent, or Firm* — The Webb Law Firm

(57) ABSTRACT

A blood draw device for use with a peripheral intravenous catheter (PIVC) includes a catheter, an introducer, an actuator movably coupled to the introducer, with the actuator configured to move relative to the introducer to move the catheter between a first position, in which the distal end of the catheter is disposed within the introducer, and a second position, in which the distal end of the catheter is disposed beyond the distal end of the introducer. The introducer defines a groove extending from the proximal end of the introducer to the distal end of the introducer. The groove is positioned within the inner volume of the introducer and closer to the bottom surface than the top surface, with the groove configured to receive a portion of the catheter during use of the blood draw device.

9 Claims, 12 Drawing Sheets

BLOOD DRAW DEVICE WITH ANTI-BUCKLING FEATURE

CROSS-REFERENCE TO RELATED APPLICATION

The present application claims priority to U.S. Provisional Application Ser. No. 63/342,366 entitled "Blood Draw Device with Anti-Buckling Feature", filed May 16, 2022, the entire disclosure of which is hereby incorporated by reference in its entirety.

BACKGROUND OF THE INVENTION

Field of the Invention

The present disclosure relates generally to blood draw devices with anti-buckling features.

Description of Related Art

Blood collection devices, when used with indwelling intravenous (IV) catheters, can include displaceable catheters that are advanced beyond the tip of the indwelling catheter for blood collection. Often, when the displaceable catheter is advanced, it can encounter an obstruction, resulting in deflection of the catheter. Examples of obstructions include the friction of the seal within the blood collection device, torturous path within an integrated catheter, pinching of the catheter tubing as it dives into the skin, thrombus, fibrin, and valves. Such deflections can reduce the ability of the displaceable catheter to extend beyond the tip of the indwelling catheter, and thus limits their use for blood collection. Accordingly, a need exists in the art for devices that limit buckling, and that ensure timely and effective blood collection.

SUMMARY OF THE INVENTION

In one aspect or embodiment, a blood draw device for use with a peripheral intravenous catheter (PIVC) includes a catheter having a proximal end, a distal end, and a sidewall therebetween defining a lumen, an introducer having a proximal end, a distal end, and a sidewall therebetween defining an inner volume configured to movably receive the catheter, with the introducer having a top surface and a bottom surface positioned opposite to the top surface, and an actuator movably coupled to the introducer. The actuator is configured to move relative to the introducer to move the catheter between a first position, in which the distal end of the catheter is disposed within the introducer, and a second position, in which the distal end of the catheter is disposed beyond the distal end of the introducer. The introducer defines a groove extending in a direction extending from the proximal end of the introducer to the distal end of the introducer. The groove is positioned within the inner volume of the introducer and closer to the bottom surface than the top surface. The groove is configured to receive a portion of the catheter during use of the blood draw device.

The groove may extend from the distal end of the introducer to the proximal end of the introducer. The groove may extend only a portion of a length extending from the distal end of the introducer to the proximal end of the introducer. The groove may be semi-spherical.

In a further aspect or embodiment, a blood draw device for use with a peripheral intravenous catheter (PIVC) includes a catheter having a proximal end, a distal end, and a sidewall therebetween defining a lumen, an introducer having a proximal end, a distal end, and a sidewall therebetween defining an inner volume configured to movably receive the catheter, with the introducer having a top surface and a bottom surface positioned opposite to the top surface, and an actuator movably coupled to the introducer. The actuator is configured to move relative to the introducer to move the catheter between a first position, in which the distal end of the catheter is disposed within the introducer, and a second position, in which the distal end of the catheter is disposed beyond the distal end of the introducer. The introducer includes a ridge positioned within the inner volume and extending radially inward, with the ridge extending in a direction extending from the proximal end of the introducer to the distal end of the introducer. The ridge is configured to engage a portion of the catheter during use of the blood draw device.

The ridge may extend from the distal end of the introducer to the proximal end of the introducer. The ridge may extend only a portion of a length extending from the distal end of the introducer to the proximal end of the introducer. The ridge may be positioned closer to the top surface than the bottom surface of the introducer. The introducer may include a first portion and a second portion attached to the first portion, with the second portion including a vertical sidewall and a horizontal wall defining at least a portion of the top surface of the introducer. The ridge may be positioned on the vertical sidewall of the second member of the introducer. The ridge may be positioned on the horizontal wall of the second member of the introducer.

In a further aspect or embodiment, a blood draw device for use with a peripheral intravenous catheter (PIVC) includes a catheter having a proximal end, a distal end, and a sidewall therebetween defining a lumen, an introducer having a proximal end, a distal end, and a sidewall therebetween defining an inner volume configured to movably receive the catheter, with the introducer including an actuator surface defining an actuator space, a top surface, and a bottom surface positioned below the top surface, and an actuator movably coupled to the introducer. The actuator is configured to move relative to the introducer to move the catheter between a first position, in which the distal end of the catheter is disposed within the introducer, and a second position, in which the distal end of the catheter is disposed beyond the distal end of the introducer. The actuator has a first portion disposed outside of the introducer and a second portion disposed in the inner volume of the introducer. The second portion of the actuator includes a lower body positioned within the actuator space. The actuator surface conforms to a top surface of the lower body of the second portion of the actuator.

The lower body of the second portion of the actuator may be circular in cross-section, with at least a portion of the actuator surface curved to conform to the top surface of the lower body of the second portion of the actuator. The actuator surface may extend at least 225 degrees around the lower body of the second portion of the actuator. The actuator surface may extend at least 300 degrees around the lower body of the second portion of the actuator.

In a further aspect or embodiment, a blood draw device for use with a peripheral intravenous catheter (PIVC) includes a catheter having a proximal end, a distal end, and a sidewall therebetween defining a lumen, an introducer having a proximal end, a distal end, and a sidewall therebetween defining an inner volume configured to movably receive the catheter, with the introducer including an actuator surface defining an actuator space, a top surface, and a bottom surface positioned below the top surface, and an actuator movably coupled to the introducer. The actuator is configured to move relative to the introducer to move the catheter between a first position, in which the distal end of the catheter is disposed within the introducer, and a second position, in which the distal end of the catheter is disposed beyond the distal end of the introducer. The actuator has a first portion disposed outside of the introducer and a second portion disposed in the inner volume of the introducer. The second portion of the actuator includes a lower body positioned within the actuator space. The device further includes a rail insert positioned between the lower body of the second portion of the actuator and the actuator surface, with the rail insert extending in a direction extending from the proximal end of the introducer to the distal end of the introducer. The rail insert is configured to engage a portion of the catheter during use of the blood draw device.

The actuator may move relative to the rail insert. The rail insert may be flexible. The rail insert may extend only a portion of a length extending from the distal end of the introducer to the proximal end of the introducer.

DESCRIPTION OF THE INVENTION

Figure 1:
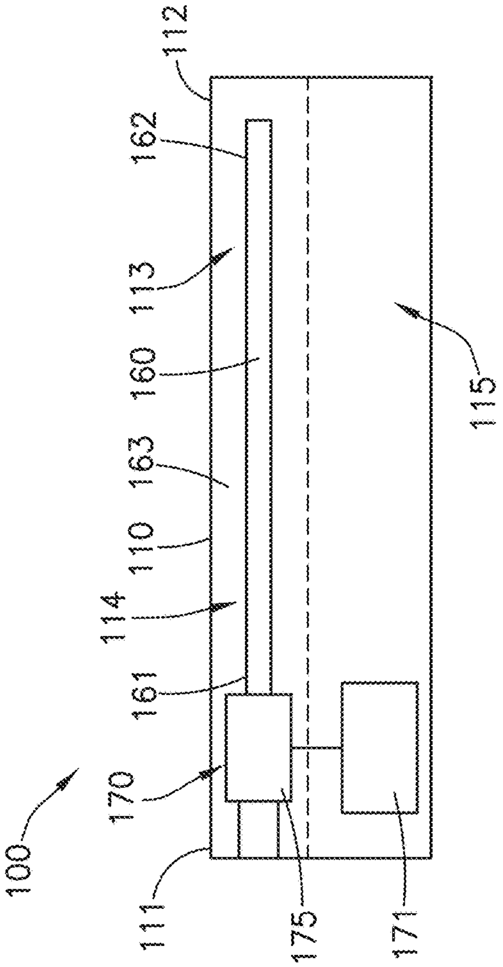
FIG. 1 is a schematic illustration of a blood draw device in a first configuration in accordance with an aspect of the present disclosure.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

U.S. Pat. No. 11,090,461, which discloses medical devices including fluid transfer devices, is incorporated by reference herein in its entirety.

Figure 2:
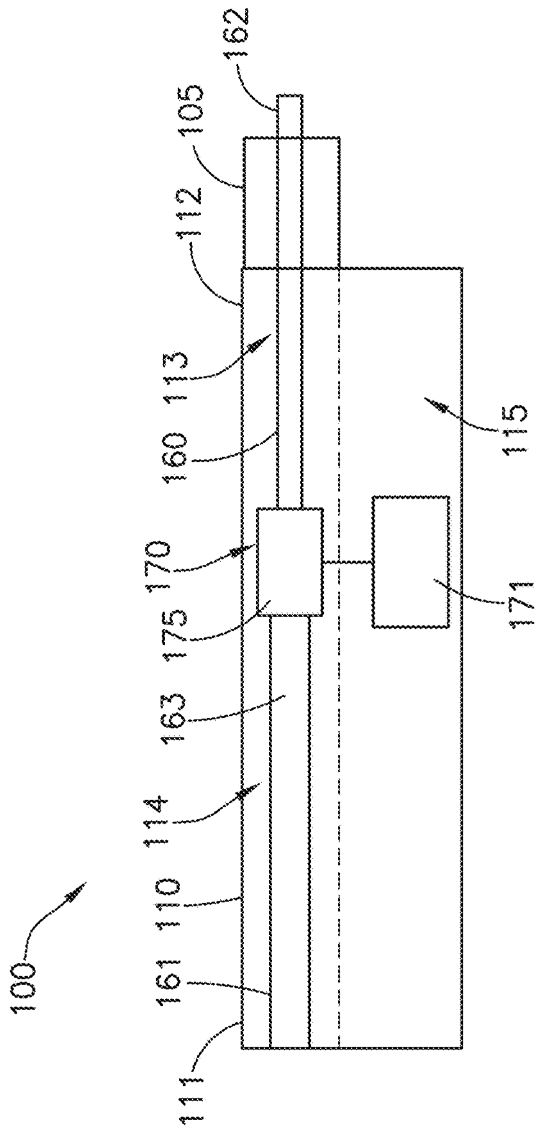
FIG. 2 is a schematic illustration of the blood draw device of FIG. 1 in a second configuration in accordance with an aspect of the present disclosure.

Referring to FIGS. 1 and 2, in one aspect or embodiment, a fluid transfer device 100 for phlebotomy through a peripheral intravenous line or catheter in a first configuration and second configuration, respectively, is shown. The fluid transfer device 100 (also referred to herein as "blood draw device" or "transfer device") can be any suitable shape, size, and/or configuration. As described in further detail herein, the transfer device 100 is configured to couple to and/or otherwise engage an indwelling peripheral intravenous catheter (PIVC) 105 to transfer fluid from (e.g., aspiration of blood) and/or transfer fluid to (e.g., infusion of a drug or substance) a portion of a patient.

The transfer device 100 includes at least an introducer 110, a catheter 160 (or cannula), and an actuator 170. The introducer 110 can be any suitable configuration. For example, in some embodiments, the introducer 110 can be an elongate member having a substantially circular cross-sectional shape. In some embodiments, the shape of the introducer 110 and/or one or more features or surface finishes of at least an outer surface of the introducer 110 can be arranged to increase the ergonomics of the transfer device 100, which in some instances can allow a user to manipulate the transfer device 100 with one hand (i.e., single-handed use).

The introducer 110 has a proximal end portion 111 and a distal end portion 112 and defines an inner volume 113. Although not shown in FIGS. 1 and 2, the proximal end portion 111 of the introducer 110 can include an opening or port configured to movably receive a portion of the catheter 160. As such, a first portion of the catheter 160 can be disposed within the inner volume 113 and a second portion of the catheter 160 can be disposed outside of the inner volume 113. The opening or port can be any suitable configuration. For example, in some embodiments, the opening and/or port can include a seal or the like configured to form a substantially fluid tight seal with an outer surface of the portion of the catheter 160 disposed therein. In other embodiments, the arrangement of the opening and/or port can be such that a user can place the catheter 160 in selective contact with a surface of the proximal end portion 111 defining the opening and/or port, which in turn can clamp and/or pinch the catheter 160 to selectively obstruct a lumen of the catheter 160, as described in further detail herein with reference to specific embodiments.

The distal end portion 112 of the introducer 110 includes and/or is coupled to a lock configured to physically and fluidically couple the introducer 110 to the PIVC 105 (see e.g., FIG. 2). For example, in some embodiments, the distal end portion 112 can include a coupler or the like such as a Luer Lok™ configured to physically and fluidically couple to an associated coupler of the lock. In some embodiments, the lock is configured to selectively engage and/or contact the PIVC 105 to couple the introducer 110 thereto. For example, in some embodiments, the shape, size, and/or arrangement of the lock is such that the lock forms three points of contact with the PIVC 105. In some embodiments, such an arrangement can provide structural rigidity and/or support to the PIVC 105 as a portion of the lock (e.g., a blunt tip cannula or the like) is inserted into a portion of the PIVC 105, as described in further detail herein.

In some aspects or embodiments, the distal end portion 112 of the introducer 110 can include and/or can be coupled to a support member or the like that is operable in placing the introducer 110 and/or transfer device 100 at a predetermined angle relative to a target surface. For example, in some embodiments, the arrangement of the lock can be such that placing a predetermined portion of the lock in contact with a target surface, in turn, places the introducer 110 and/or transfer device 100 at a predetermined and/or desired angle relative to the target surface. In other embodiments, a support member and/or the like can be coupled to the distal end portion 112 of the introducer 110 and configured to place the introducer 110 and/or transfer device 100 at the predetermined and/or desired angle relative to the target surface. In some instances, the target surface can be a cutaneous surface of a body through which the PIVC 105 is inserted (e.g., an outer surface of a patient's arm or the like). In some aspects or embodiments, the predetermined angle can be, for example, between about 0° and about 30°, between about 4° and about 15°, between about 8° and about 10°, or any other suitable angle.

In some aspects or embodiments, the distal end portion 112 of the introducer 110 (and/or the lock) can include a seal or the like that can be transferred from a sealed configuration to a substantially open configuration to place at least a portion of the inner volume 113 in fluid communication with the lock. The seal can include a back flow prevention mechanism such as a one-way valve or the like that can allow, for example, the catheter 160 to be advanced in the distal direction therethrough while limiting and/or substantially preventing a fluid flow outside the catheter 160 in the proximal direction through the seal.

As described above, the introducer 110 defines the inner volume 113, which extends between the proximal end portion 111 and the distal end portion 112. The inner volume 113 has and/or defines a first portion 114 configured to receive a first portion 171 of the actuator 170 and a second portion 115 configured to receive the catheter 160 and a second portion 175 of the actuator 170, as shown in FIGS. 1 and 2. More specifically, an inner surface of the introducer 110 that defines the inner volume 113 can have, for example, a tortuous cross-sectional shape (not shown in FIGS. 1 and 2) such that an axis defined by the first portion 114 of the inner volume 113 is parallel to and offset from an axis defined by the second portion 115 of the inner volume 113. In this manner, the first portion 114 of the inner volume 113 can be spaced apart from the second portion 115 of the inner volume 113 without being fluidically isolated therefrom. The first portion 114 of the inner volume 113 can extend through a wall of the introducer 110. In other words, the introducer 110 can define a slot, channel, track, opening, and/or the like that is in fluid communication with the first portion 114 of the inner volume 113. Conversely, the second portion 115 of the inner volume 113 can be entirely defined and/or enclosed (at least in the circumferential direction) by the introducer 110. Moreover, in some aspects or embodiments, the tortuous cross-sectional shape of the inner volume 113 is such that the second portion 115 cannot be viewed (e.g., is out of the line of sight) via the slot or the like in fluid communication with the first portion 114 of the inner volume 113, which in turn can limit and/or substantially prevent contamination of the catheter 160 disposed therein.

The catheter 160 of the transfer device 100 includes a proximal end portion 161 and a distal end portion 162 and defines a lumen 163 that extends through the proximal end portion 161 and the distal end portion 162. The catheter 160 is movably disposed within the second portion 115 of the inner volume 113 defined by the introducer 110 and is coupled to the actuator 170. The catheter 160 can be moved (e.g., via movement of the actuator 170) between a first position and a second position to transition the transfer device 100 between the first configuration and the second configuration, respectively. More specifically, at least the distal end portion 162 of the catheter 160 is disposed within the second portion 115 of the inner volume 113 when the catheter 160 is in the first position (FIG. 1), and at least a portion of the catheter 160 extends through the PIVC 105 to place the distal end of the catheter 160 in a distal position relative to a portion of the PIVC 105 when the catheter 160 is in the second position (FIG. 2). Although not shown in FIGS. 1 and 2, in some embodiments, the transfer device 100 can include a secondary catheter or the like that is coupled to the actuator 170 and in fluid communication with the catheter 160. In such embodiments, the secondary catheter can be, for example, disposed in a proximal position relative to the catheter 160 and can be configured to extend through the opening and/or port defined by the proximal end portion 111 of the introducer 110. In this manner, a proximal end portion of the secondary catheter can be coupled to a vacuum (air or liquid) source, a fluid reservoir, fluid source, syringe, and/or the like, which in turn places the catheter 160 in fluid communication therewith. Moreover, in embodiments including the secondary catheter, the catheter 160 can be entirely disposed within the introducer 110 when the catheter 160 is in the first position.

The catheter 160 can be any suitable shape, size, and/or configuration. For example, in some embodiments, at least a portion of the catheter 160 can have an outer diameter (e.g., between a 10-gauge and a 30-gauge) that is substantially similar to or slightly smaller than an inner diameter defined by a portion of the lock coupled to the distal end portion 112 of the introducer 110. In this manner, an inner surface of the portion of the lock can guide the catheter 160 as the catheter 160 is moved between the first position and the second position. Such an arrangement can limit and/or can substantially prevent bending, deforming, and/or kinking of a portion of the catheter 160 as the portion is moved between the first position and the second position. The catheter 160 can have a length that is sufficient to place a distal surface of the catheter 160 in a desired position relative to a distal surface of the PIVC 105 when the catheter 160 is in the second position. In other words, the length of the catheter 160 can be sufficient to define a predetermined and/or desired distance between the distal surface of the catheter 160 and the distal surface of the PIVC 105 when the catheter 160 is in the second position. In some instances, placing the distal surface of the catheter 160 at the predetermined and/or desired distance from the distal surface of the PIVC 105 can, for example, place the distal surface of the catheter 160 in a desired position within a vein, as described in further detail herein.

The catheter 160 can be formed from any suitable material or combination of materials, which in turn can result in the catheter 160 having any suitable stiffness or durometer. In some embodiments, at least a portion of the catheter 160 can be formed of a braided material or the like, which can change, modify, and/or alter the flexibility of the catheter 160 in response to a bending force or the like. In some aspects or embodiments, forming the catheter 160 of the braided material or the like can reduce a likelihood of kinking and/or otherwise deforming the catheter 160 in an undesired manner. In addition, forming at least a portion of the catheter 160 of a braided material can result in a compression and/or deformation in response to a compression force exerted in a direction of a longitudinal centerline defined by the catheter 160 (e.g., an axial force or the like). In this manner, the catheter 160 can absorb a portion of force associated with, for example, impacting an obstruction or the like. As described in further detail herein, in some instances, at least a portion of the catheter 160 can deform in response to the force associated with impacting such an obstruction or the like.

The actuator 170 of the transfer device 100 can be any suitable shape, size, and/or configuration. As described above, the actuator 170 includes the first portion 171 movably disposed within the first portion 114 of the inner volume 113 and the second portion 175 movably disposed within the second portion 115 of the inner volume 113 and coupled to the catheter 160. Although not shown in FIGS. 1 and 2, the actuator 170 can have a cross-sectional shape that is associated with and/or otherwise corresponds to the cross-sectional shape of the inner volume 113 (e.g., the tortuous cross-sectional shape). Thus, an axis defined by the first portion 171 of the actuator 170 is parallel to and offset from an axis defined by the second portion 175 of the actuator 170.

The arrangement of the actuator 170 and the introducer 110 is such that the first portion 171 extends through the slot or the like in fluid communication with the first portion 114 of the inner volume 113. As such, a first region of the first portion 171 of the actuator 170 is disposed outside of the introducer 110 and a second region of the first portion 171 of the actuator 170 is disposed in the first portion 114 of the inner volume 113. In this manner, a user can engage the first region of the first portion 171 of the actuator 170 and can move the actuator 170 relative to the introducer 110 to move the catheter 160 coupled to the second portion 175 of the actuator 170 between the first position and the second position. Although not shown in FIGS. 1 and 2, in some embodiments, the first portion 171 of the actuator 170 can include a tab, protrusion, and/or surface that is in contact with an outer surface of the introducer 110. In such embodiments, the outer surface of the introducer 110 can include, for example, a set of ribs, ridges, bumps, grooves, and/or the like along which the tab, protrusion, and/or surface of the first portion 171 advances when the actuator 170 is moved relative to the introducer 110 which in turn, produces a haptic output or feedback (acoustic, tactile, and visual) which can provide an indication associated with a position of the distal end portion 162 of the catheter 160 to the user.

In some aspects or embodiments, the arrangement of the first portion 171 of the 170 and the outer surface of the introducer 110 is such that the actuator 170 is disposed at an angle relative to the introducer 110. That is to say, the contact between the first portion 171 of the actuator 170 and the outer surface of the introducer 110 tilts the actuator 170 relative to the introducer 110. Accordingly, a longitudinal centerline of the actuator 170 can be nonparallel to a longitudinal centerline of the introducer 110. Furthermore, with the actuator 170 coupled to the proximal end portion 161 of the catheter 160, angling and/or tilting the actuator 170 results in a force (e.g., a pre-load force or the like) exerted on the catheter 160 that is sufficient to bend at least a portion of the catheter 160 (e.g., the catheter 160 is placed in a biased configuration), as described in further detail herein.

In some aspects or embodiments, the transfer device 100 can be disposed in the first configuration prior to use (e.g., shipped, stored, prepared, etc., in the first configuration). In use, a user can manipulate the transfer device 100 to couple the introducer 110 to the indwelling PIVC 105 (e.g., via the lock coupled to and/or assembled with the introducer 110). With the transfer device 100 coupled to the PIVC 105, the user can engage the first portion 171 of the actuator 170 to move the actuator 170 relative to the introducer 110, which in turn moves the catheter 160 from the first position (e.g., disposed within the introducer 110) toward the second position. The arrangement of the actuator 170 and the introducer 110 is such that advancing the actuator 170 relative to the introducer 110 produces a haptic output and/or feedback configured to provide an indicator associated with the position of the distal end portion 162 of the catheter 160 relative to the introducer 110 and/or the PIVC 105 to the user. For example, based on the haptic feedback, or any other suitable indicator, the user can place the catheter 160 in the second position such that the distal surface of the catheter 160 extends a desired distance beyond the distal surface of the PIVC 105, as described above.

With the catheter 160 in the second position (e.g., with the transfer device 100 in the second configuration shown in FIG. 2), the user can establish fluid communication between a fluid reservoir, fluid source, syringe, and/or the like, and the catheter 160. For example, as described above, in some embodiments, the user can couple the secondary catheter (not shown) to the fluid reservoir, fluid source, syringe, and/or the like. Although described as establishing fluid communication between the catheter 160 and the fluid reservoir or fluid source after placing the catheter 160 in the second position, in other embodiments, the user can establish fluid communication between the catheter 160 and the fluid reservoir or fluid source prior to moving the actuator 170 relative to the introducer 110. With the catheter 160 in fluid communication with the fluid reservoir and/or fluid source, the transfer device 100 can then transfer a fluid from the patient or transfer a fluid to the patient via the catheter 160 extending through and beyond the PIVC 105.

In some instances, the catheter 160 can impact an obstruction or the like as the user advances the catheter 160 (via the actuator 170) from the first position to the second position. In some such instances, the catheter 160 can be configured to bend, deform, and/or otherwise reconfigure in response to a force exerted by the user. That is to say, a force (e.g., an activation or actuation force) exerted by the user on the actuator 170 that otherwise is sufficient to move the catheter 160 toward the second position results in a deflection, deformation, and/or reconfiguration of at least a portion of the catheter 160 when the catheter 160 impacts an obstruction or the like. Moreover, with at least a portion of the catheter 160 being pre-loaded (e.g., bent, bowed, biased, deflected, and/or deformed in response to the angle of the actuator 170, as described above), the deflection, deformation, and/or reconfiguration of the portion of the catheter 160 can be predetermined, anticipated, and/or the like.

Referring to FIGS. 3-9, a fluid transfer device 200 according to a further embodiment is shown. The fluid transfer device 200 (also referred to herein as "blood draw device" or "transfer device") can be any suitable shape, size, or configuration and can be coupled to a PIVC (not shown in FIGS. 3-9), for example, via a lock and/or adapter. As described in further detail herein, a user can transition the transfer device 200 from a first configuration to a second configuration to advance a catheter through an existing, placed, and/or indwelling PIVC (i.e., when the transfer device 200 is coupled thereto) such that at least an end portion of the catheter is disposed in a distal position relative to the PIVC. Moreover, with peripheral intravenous lines each having a shape, size, and/or configuration that can vary based on, for example, a manufacturer of the PIVC and/or its intended usage, the transfer device 200 can be arranged to allow the transfer device 200 to be coupled to a PIVC having any suitable configuration and, subsequently, to advance at least a portion of a catheter through the PIVC substantially without kinking, snagging, breaking, and/or otherwise reconfiguring the catheter in an undesirable manner. In addition, the transfer device 200 can be manipulated by a user to place a distal surface of the catheter a predetermined and/or desired distance beyond a distal surface of the PIVC to be disposed within a portion of a vein that receives a substantially unobstructed flow of blood.

Figure 3:
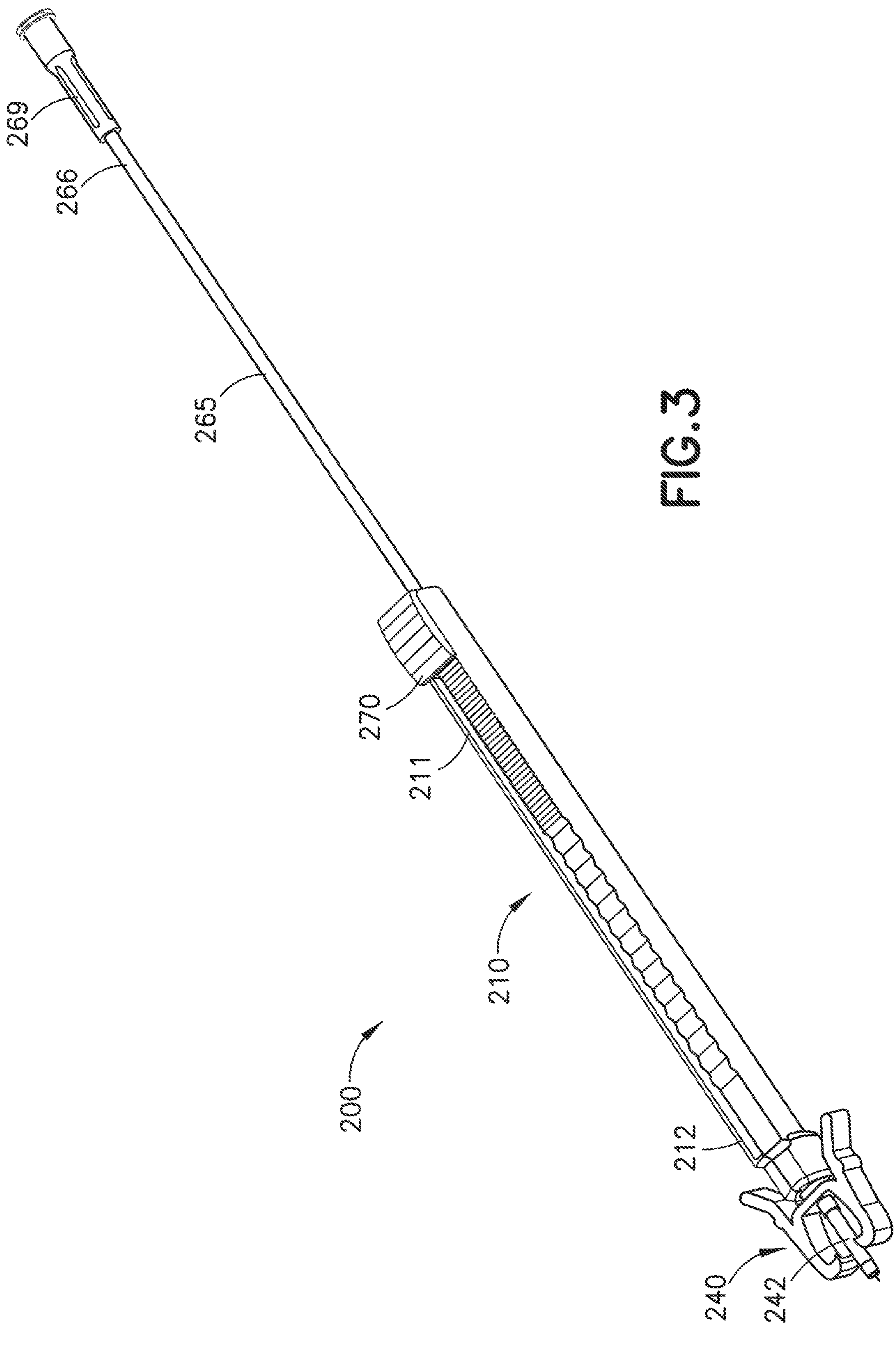
FIG. 3 is a perspective view of a blood draw device in accordance with an aspect of the present disclosure.
Figure 4:
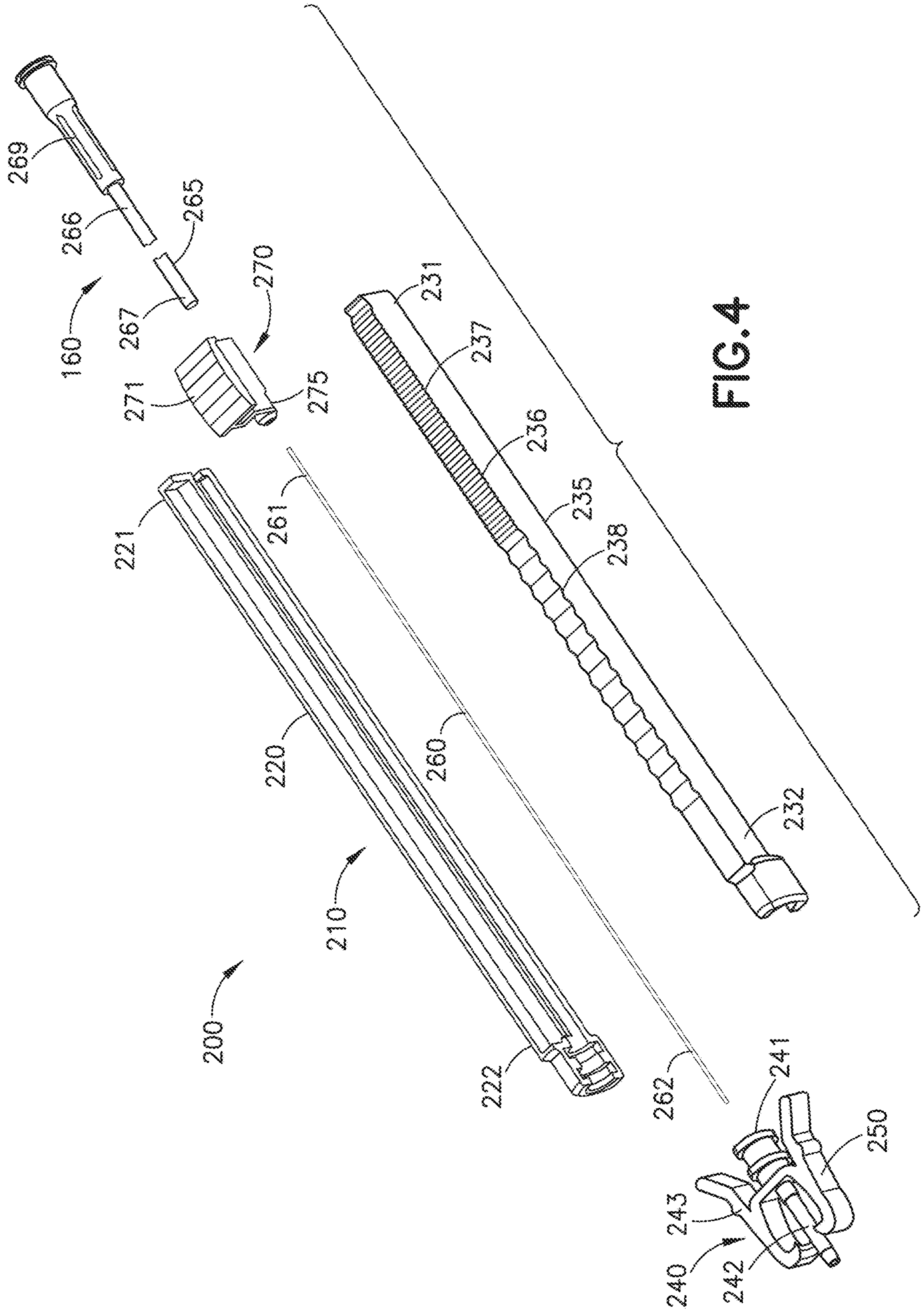
FIG. 4 is an exploded perspective view of the blood draw device of FIG. 3.
Figure 5:
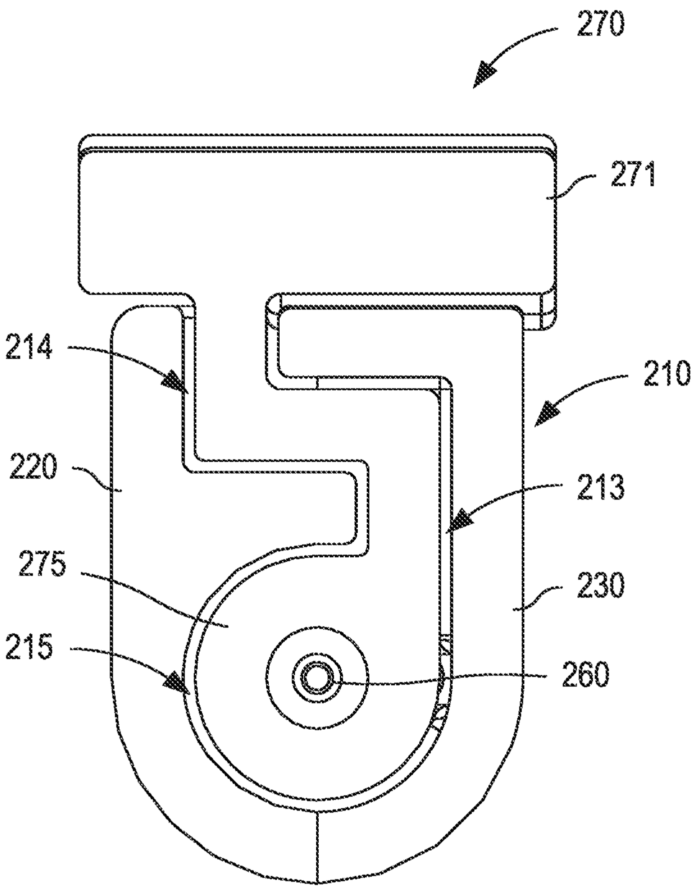
FIG. 5 is a partial rear view of the blood draw device of FIG. 3.
Figure 6:
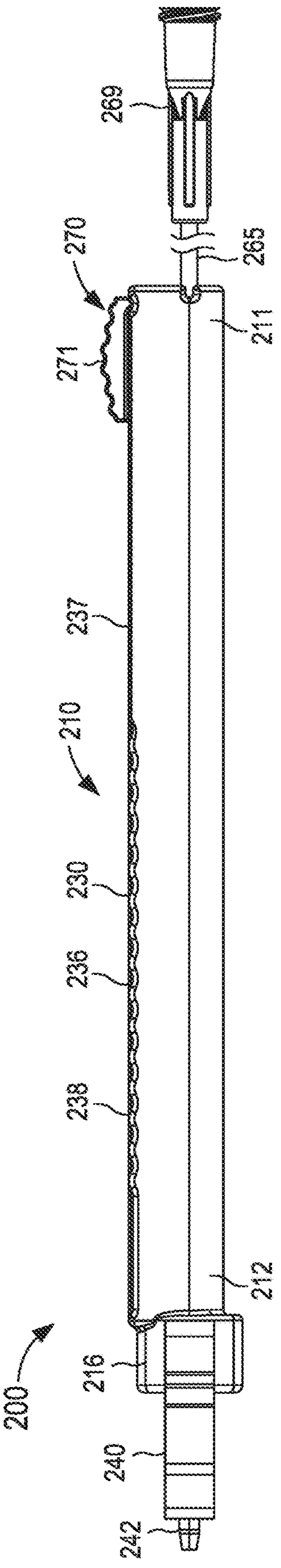
FIG. 6 is a side view of the blood draw device of FIG. 3.

Referring to FIGS. 3-5, the transfer device 200 includes an introducer 210, a lock 240, a catheter 260, a secondary catheter 265, and an actuator 270. The introducer 210 can be any suitable shape, size, or configuration. For example, in some embodiments, the introducer 210 can be an elongate member having a substantially circular cross-sectional shape. In some embodiments, the shape of the introducer 210 and/or one or more features or surface finishes of at least an outer surface of the introducer 210 can be arranged to increase the ergonomics of the transfer device 200, which, in some instances, can allow a user to manipulate the transfer device 200 with one hand (i.e., single-handed use).

Referring to FIGS. 3-9, the introducer 210 of the transfer device 200 includes a first member 220 and a second member 230 that are coupled to collectively form the introducer 210. The first member 220 includes a proximal end portion 221 and a distal end portion 222. The actuator 270 includes a first portion 271, a second portion 275, and a wall 277 extending therebetween. The first portion 271 of the actuator 270 is at least partially disposed within the first portion 214 of the inner volume defined by the introducer 210, and the second portion 275 of the actuator 270 is disposed within a second portion 215 of the inner volume. The first portion 271 of the actuator 270 can be engaged and/or manipulated by a user (e.g., by a finger or thumb of the user) to move the actuator 270 relative to the introducer 210. The first portion 271 of the actuator 270 may include a set of ridges and/or any suitable surface finish that can, for example, increase the ergonomics of the actuator 270 and/or transfer device 200. The first portion 271 of the actuator 270 includes a tab 273 disposed at or near a proximal end portion of an engagement member 272. The tab 273 can be any suitable tab, rail, ridge, bump, protrusion, knob, roller, slider, etc. The tab 273 is configured to selectively engage ribs 237 on an outer surface of the second member 230 of the introducer 210. A proximal end portion 211 of the introducer 210 defines an opening 217.

Figure 7:
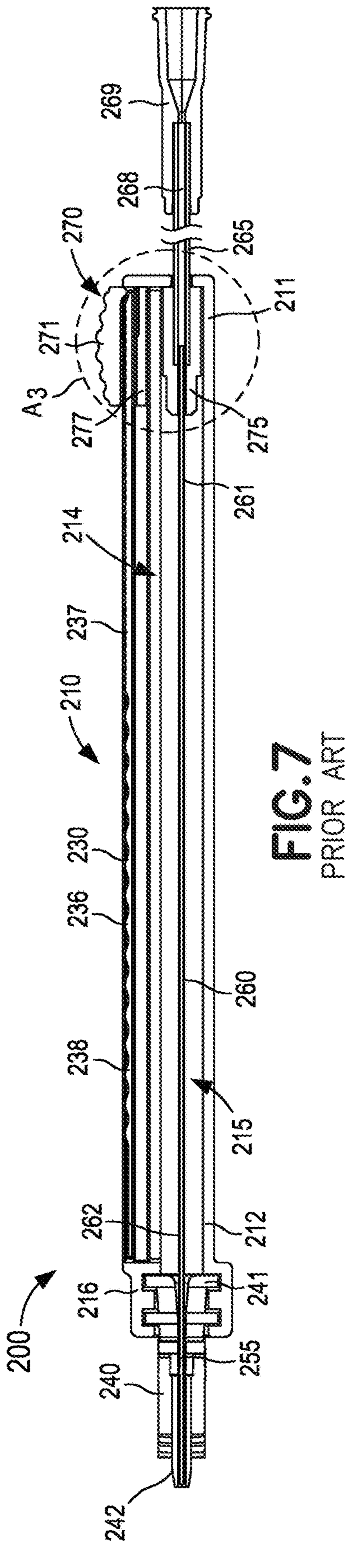
FIG.7 PRIOR ART
FIG. 7 is a cross-sectional view of a prior art blood draw device.
Figure 8:
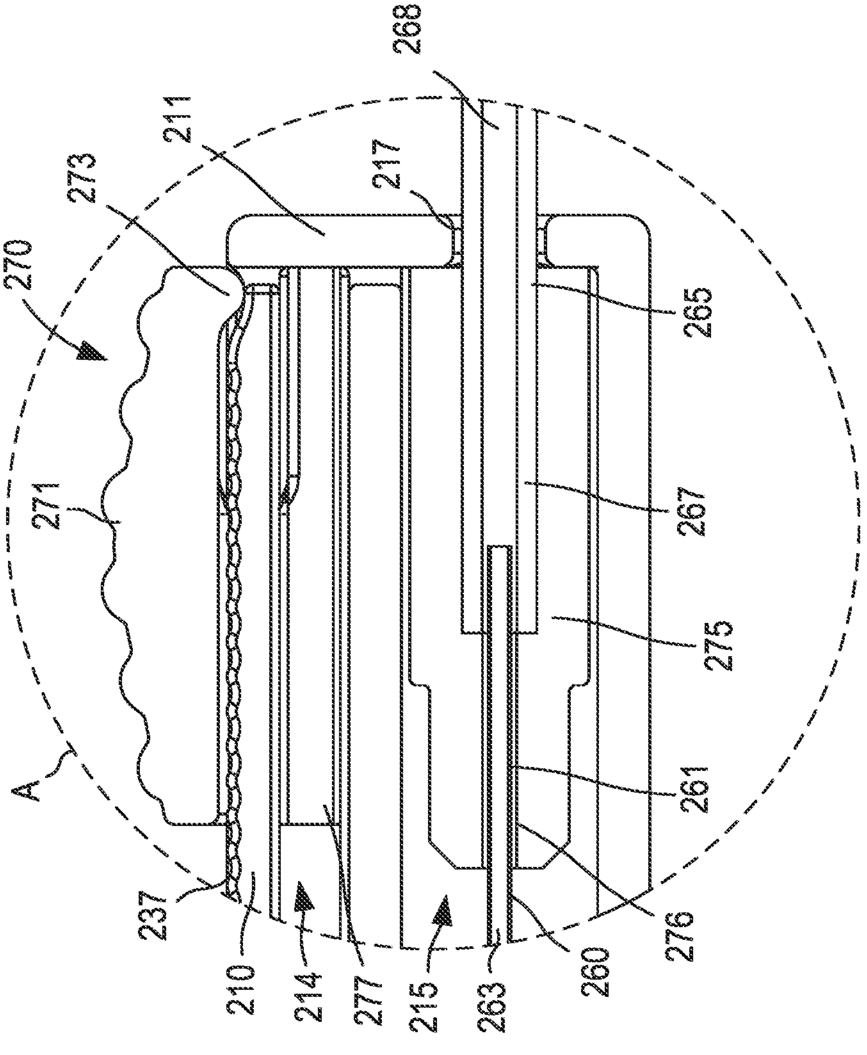
FIG.8 PRIOR ART
FIG. 8 is an enlarged cross-sectional view of Area A shown in FIG. 7.
Figure 9:
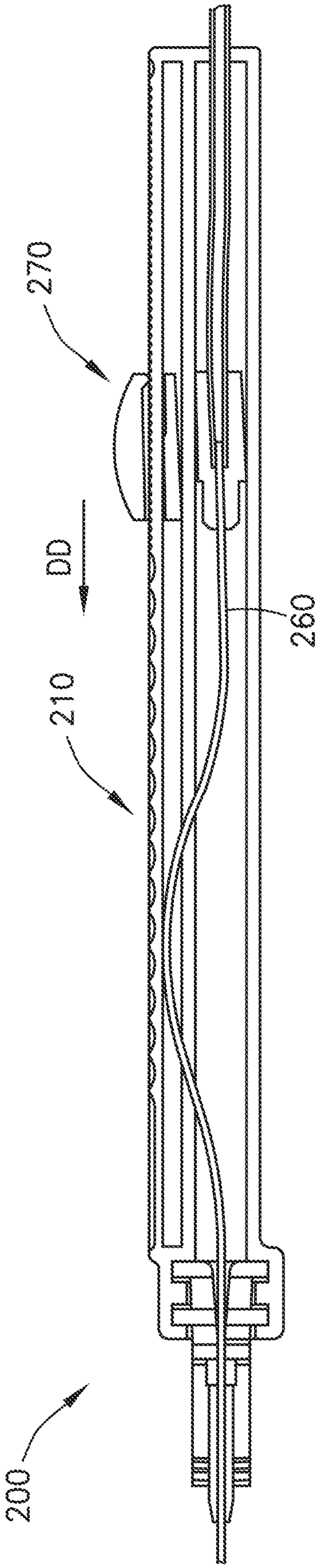
FIG. 9 PRIOR ART
FIG. 9 is a cross-sectional view of a prior art blood draw device, showing a catheter with a deflected position.

Referring to FIGS. 7-9, conventionally, the second portion 275 defines an opening 276 configured to receive a proximal end portion 261 of the catheter 260 and a distal end portion 267 of the secondary catheter 265. A portion of the secondary catheter 265 is disposed in the opening 217 defined by the introducer such that the distal end portion 267 is at least partially disposed in the second portion 215 of the inner volume and coupled to the second portion 275 of the actuator 270 while the proximal end portion 266 of the secondary catheter 265 is disposed outside of the introducer 210. The proximal end portion 266 of the secondary catheter 265 is coupled to and/or otherwise includes a coupler 269. The coupler 269 is configured to physically and fluidically couple the secondary catheter 265 to any suitable device such as, for example, a fluid reservoir, fluid source, syringe, evacuated container holder (e.g., having a sheathed needle or configured to be coupled to a sheathed needle), pump, and/or the like. Positioning the distal end portion 267 of the secondary catheter 265 within the opening 276 of the actuator 270 limits a minimum height or diameter of the second portion 275 of the actuator 270. For example, in the conventional arrangement of the actuator 270 of FIGS. 7 and 8, the actuator may be overmolded onto the secondary catheter 265, which necessitates a predetermined wall thickness of material of the actuator 270 surrounding the secondary catheter 265. As shown in FIG. 9, a healthcare worker can exert a force on the actuator 270 to move the actuator 270 in a distal direction relative to the introducer 210, which in turn moves the catheter 260 toward its second position (e.g., the distal position), as indicated by the arrow DD. In some instances, however, the catheter 260 (e.g., the distal end of the catheter 260) may encounter or impact an obstruction or the like that hinders or prevents further distal movement of the catheter 260. With the distal end of the catheter 260 in contact with the obstruction, the force exerted by the healthcare worker on the actuator 270 (e.g., in the DD direction) results in a "clutching" (e.g., deflection, deformation, bending, bowing, etc.) of the catheter 260.

Figure 10:
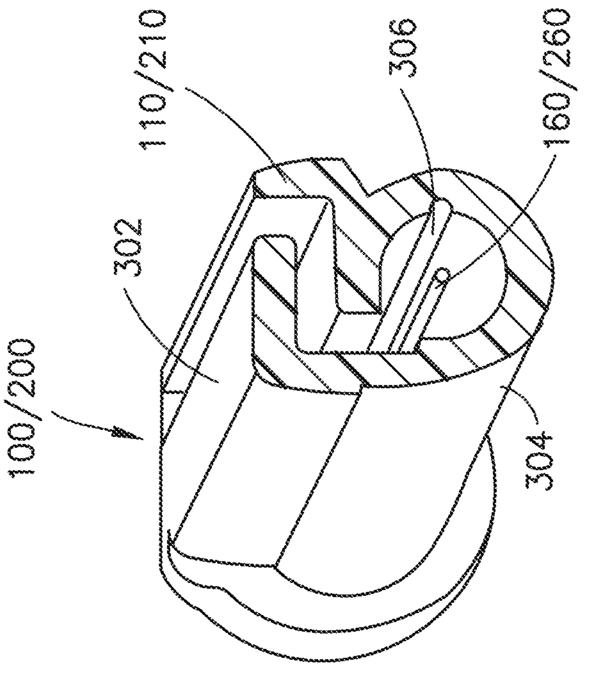
FIG. 10 is a cross-sectional view of a blood draw device in accordance with an aspect of the present disclosure.

Referring to FIG. 10, in one aspect or embodiment of the present application, the introducer 110, 210 of either of device 100 or device 200 includes a top surface 302 and a bottom surface 304 positioned opposite to the top surface 302 and defines a groove 306 extending in a direction extending from the proximal end 111, 211 of the introducer 110, 210 to the distal end 112, 212 of the introducer 110, 210. The groove 306 is positioned within the inner volume 113 of the introducer 110, 210 and closer to the bottom surface 304 than the top surface 302. The groove 306 is configured to receive a portion of the catheter 160, 260 during use of the blood draw device 100, 200. More specifically, the groove 306 is configured to receive a portion of the catheter 160, 260 to keep the catheter 160, 260 from bowing in an upward direction and also preventing the catheter 160, 260 from moving into a slot between the first portion 114, 214 and the second portion 115, 215 of the introducer 110, 210. In some aspects or embodiments, the groove 306 extends from the distal end 112, 212 of the introducer 110, 210 to the proximal end 111, 211 of the introducer 110, 210. In some aspects or embodiments, the groove 306 extends only a portion of a length extending from the distal end 112, 212 of the introducer 110, 210 to the proximal end 111, 211 of the introducer 110, 210. The groove 306 is semi-spherical, although other suitable shapes may be utilized.

Figure 11:
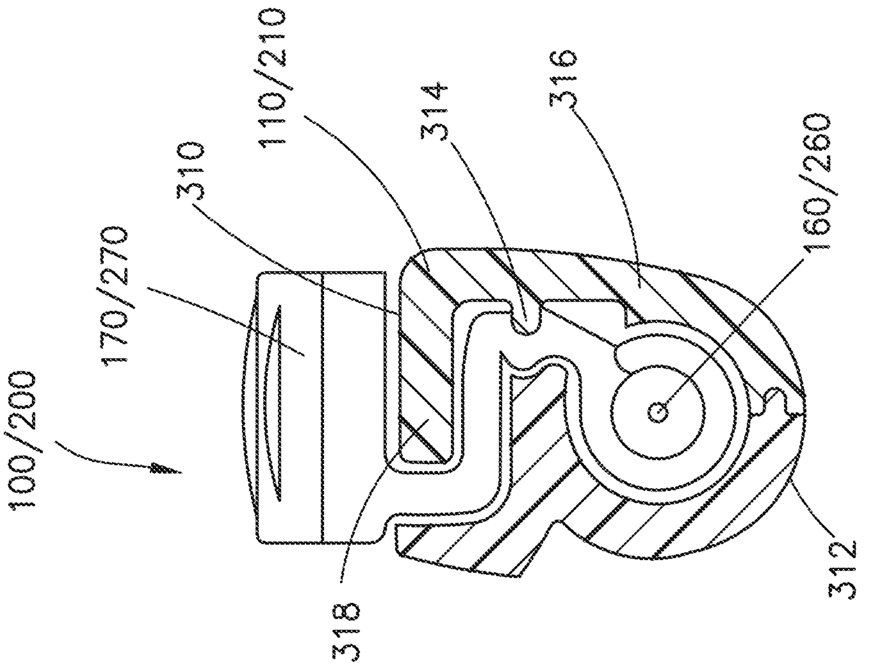
FIG. 11 is a cross-sectional view of a blood draw device in accordance with a further aspect of the present disclosure.
Figure 12:
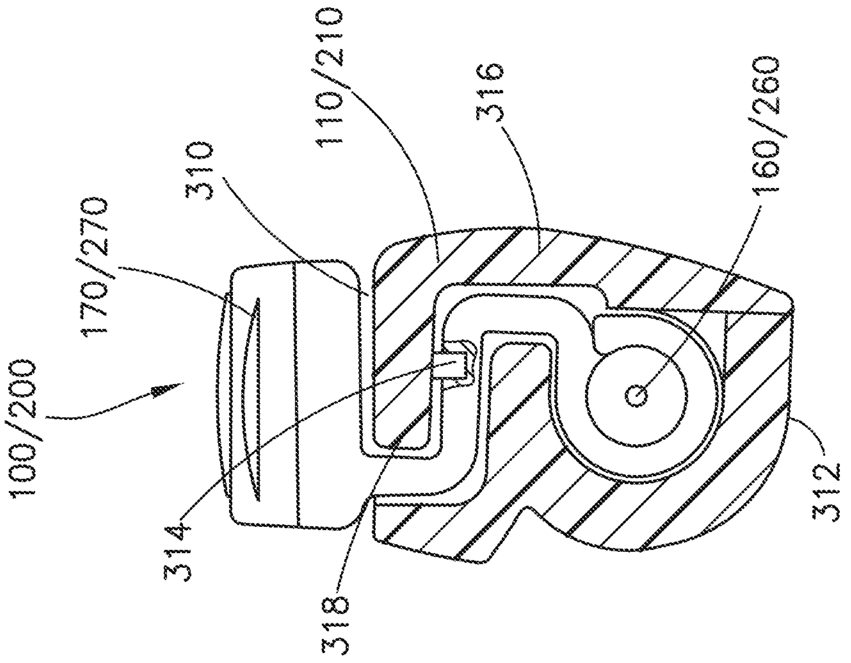
FIG. 12 is a cross-sectional view of a blood draw device in accordance with a further aspect of the present disclosure.

Referring to FIGS. 11 and 12, in one aspect or embodiment of the present application, the introducer 110, 210 of either of device 100 or device 200, includes a top surface 310 and a bottom surface 312 positioned opposite to the top surface 310 and a ridge 314 positioned within the inner volume 113 and extending radially inward. The ridge 314 extends in a direction extending from the proximal end 111, 211 of the introducer 110, 210 to the distal end 112, 212 of the introducer 110, 210. The ridge 314 is configured to engage a portion of the catheter 160, 260 during use of the blood draw device 100, 200. In some aspects or embodiments, the ridge 314 extends from the distal end 112, 212 of the introducer 110, 210 to the proximal end 111, 211 of the introducer 110, 210. In some aspects or embodiments, the ridge 314 extends only a portion of a length extending from the distal end 112, 212 of the introducer 110, 210 to the proximal end 111, 211 of the introducer 110, 210. The ridge 314 is positioned closer to the top surface 310 than the bottom surface 312, although other suitable arrangements may be utilized. The second portion 115, 214 of the introducer 110, 210 includes a vertical sidewall 316 and a horizontal sidewall 318 defining at least a portion of the top surface 310 of the introducer 110, 210. In one aspect or embodiment, as shown in FIG. 11, the ridge 314 is positioned on the vertical sidewall 316 of the second portion 115, 215 of the introducer 110, 210. In one aspect or embodiment, as shown in FIG. 12, the ridge 314 is positioned on the horizontal sidewall 318 of the second portion 115, 215 of the introducer 110, 210. The ridge 314 is configured to engage the catheter 160, 260 as the catheter 160, 260 slides up the introducer 110, 210 during use of the blood transfer device 100,200. The ridge may be flat, angled downward in a direction extending from the top surface of the introducer 110, 210 toward the bottom surface of the introducer 110, 210, or curved, although other suitable shapes may be utilized.

Figure 13:
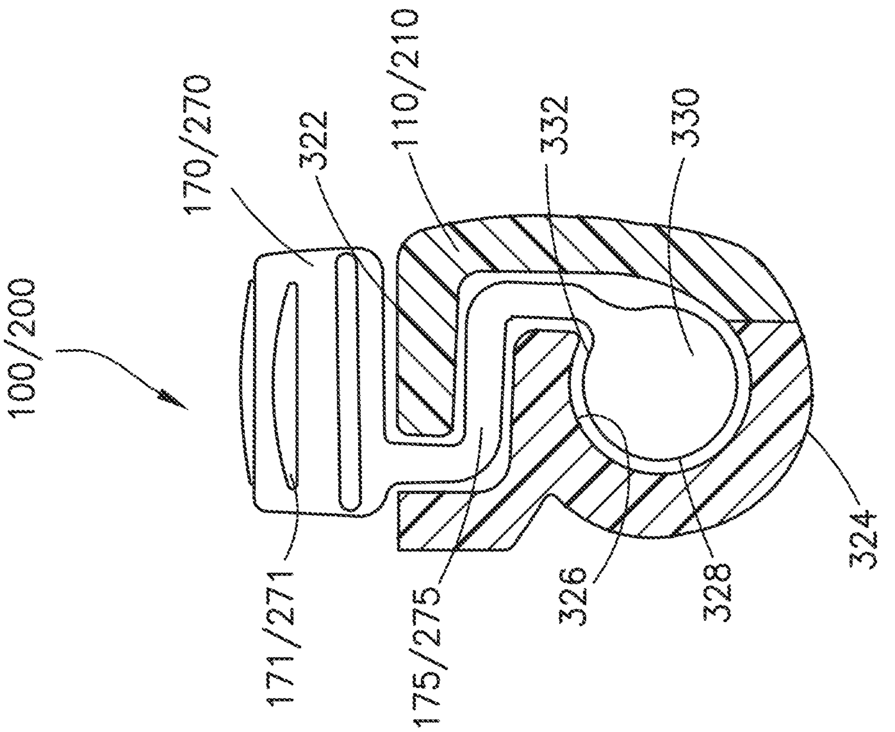
FIG. 13 is a cross-sectional view of a blood draw device in accordance with an aspect of the present disclosure.

Referring to FIG. 13, in one aspect or embodiment of the present application, the introducer 110, 210 of either of device 100 or device 200 includes a top surface 322 and a bottom surface 324 positioned below the top surface 322 and an actuator surface 326 defining an actuator space 328. The second portion 175, 275 of the actuator 170, 270 includes a lower body 330 positioned within the actuator space. The actuator surface 326 conforms to a top surface 332 of the lower body 330 of the second portion 175, 275 of the actuator 170, 270. As noted above, the first portion 171, 271 of the actuator 170, 270 is disposed outside of the introducer 110, 210, and the second portion 175, 275 of the actuator 170, 270 is disposed in the inner volume 113 of the introducer 110, 210. In some aspects or embodiments, the lower body 330 of the second portion 175, 275 of the actuator 170, 270 is circular in cross-section, and at least a portion of the actuator surface 326 is curved to conform to the top surface 332 of the lower body 330 of the second portion 175, 275 of the actuator 170, 270. In some aspects or embodiments, the actuator surface 326 extends at least 225 degrees around the lower body 330 of the second portion 175, 275 of the actuator 170, 270. In some aspects or embodiment, the actuator surface 326 extends at least 300 degrees around the lower body 330 of the second portion 175, 275 of the actuator 170, 270. The actuator surface 326 is configured to engage the catheter 160, 260 during use of the device 100, 200 such that the catheter 160, 260 remains within the actuator space 328 as the catheter 160, 260 is advanced. Confinement of the catheter 160, 260 within the smaller diameter of the actuator space 328 is configured to reduce the amount of bending of the catheter 160, 260 thereby reducing the chances of kinking or buckling of the catheter 160, 260.

Figure 14:
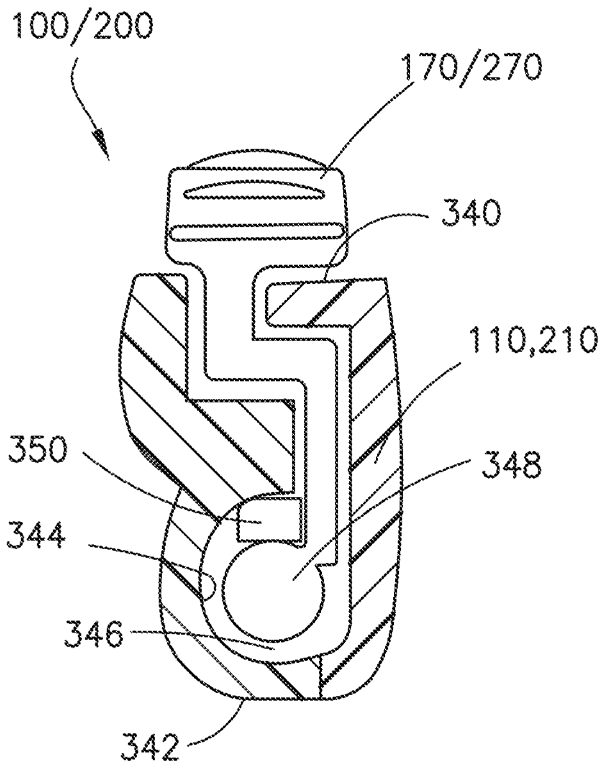
FIG. 14 is a cross-sectional view of a blood draw device in accordance with a further aspect of the present disclosure.
Figure 15:
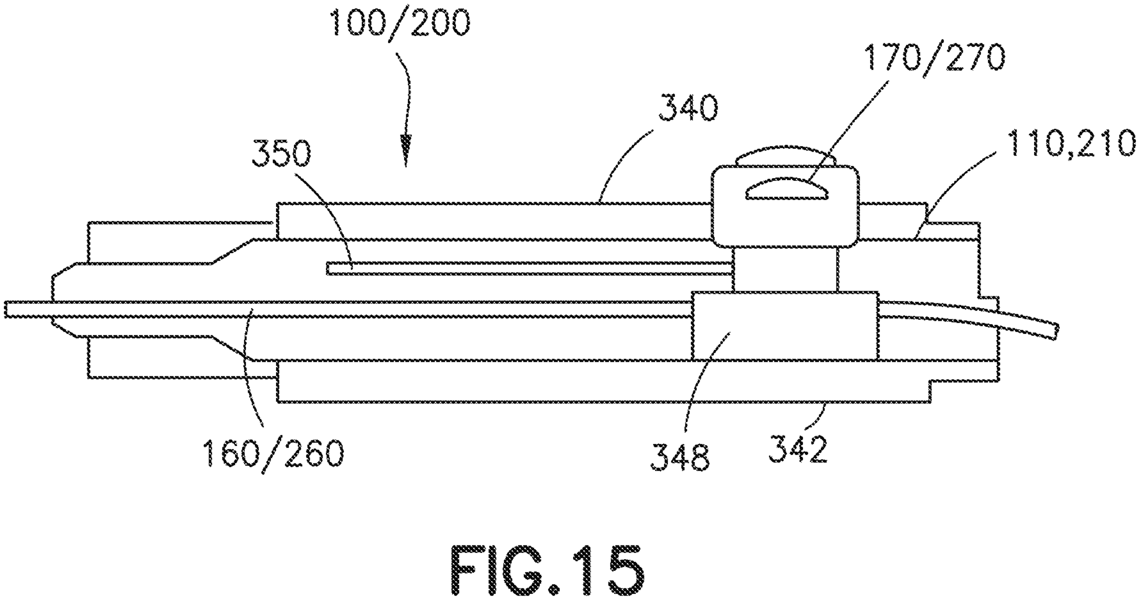
FIG. 15 is a cutaway view of the blood draw device of FIG. 14.

Referring to FIGS. 14 and 15, in one aspect or embodiment of the present application, the introducer 110, 210 of either of device 100 or device 200 includes a top surface 340, a bottom surface 342 positioned below the top surface 340, and an actuator surface 344 defining an actuator space 346. The second portion 175, 275 of the actuator 170, 270 includes a lower body 348 positioned within the actuator space 346. As shown in FIGS. 14 and 15, the device 100, 200 may also include a rail insert 350 positioned between the lower body 348 of the second portion 175, 275 of the actuator 170, 270 and the actuator surface 344. The rail insert 350 extends in a direction extending from the proximal end 111, 211 of the introducer 110, 210 to the distal end 112, 212 of the introducer 110, 210. The rail insert 350 is configured to engage a portion of the catheter 160, 260 during use of the blood draw device 100, 200. In some aspects or embodiments, the actuator 170, 270 moves relative to the rail insert 350. The rail insert 350 may be connected or fixed relative to the introducer 110, 210 or may float or move relative to both the introducer 110, 210 and the actuator 170, 270. In some aspects or embodiments, the rail insert 350 is flexible. The rail insert 350 may be as flexible as the catheter 160, 260 or less flexible than the catheter 160, 260 and more flexible than the introducer 110, 210. The rail insert 350 extends only a portion of a length extending from the distal end 112, 212 of the introducer 110, 210 to the proximal end 111, 211 of the introducer 110, 210, although other suitable lengths and arrangements may be utilized.

Figure 16:
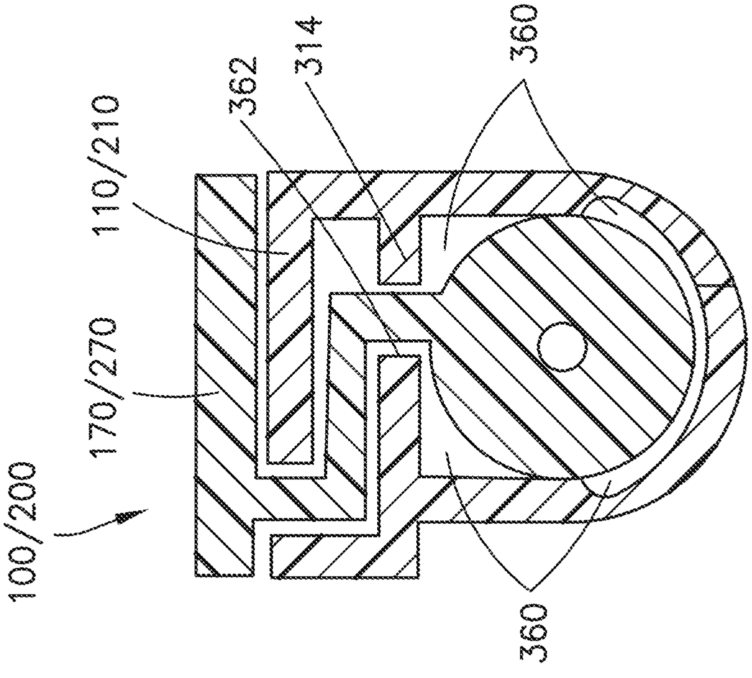
FIG. 16 is a cross-sectional view of a blood draw device in accordance with a further aspect of the present disclosure.

Referring to FIG. 16, in one aspect or embodiment of the present application, the introducer 110, 210 of either of device 100 or device 200, is similar to the embodiments of FIGS. 11 and 12. However, the first portion 114, 214 and/or the second portion 115, 215 of the introducer 110, 210 may define one or more tracks 360 configured to prevent the catheter 160, 260 from escaping from a gap 362 between the first portion 114, 214 and the second portion 115, 215 through which the actuator 170, 270 extends. The tracks 360 may be recessed portions defined by the first portion 114, 214 and/or the second portion 115, 215 of the introducer 110, 210 and may include hooked and/or curved portions configured to restrain the catheter 160, 260.

Figure 17:
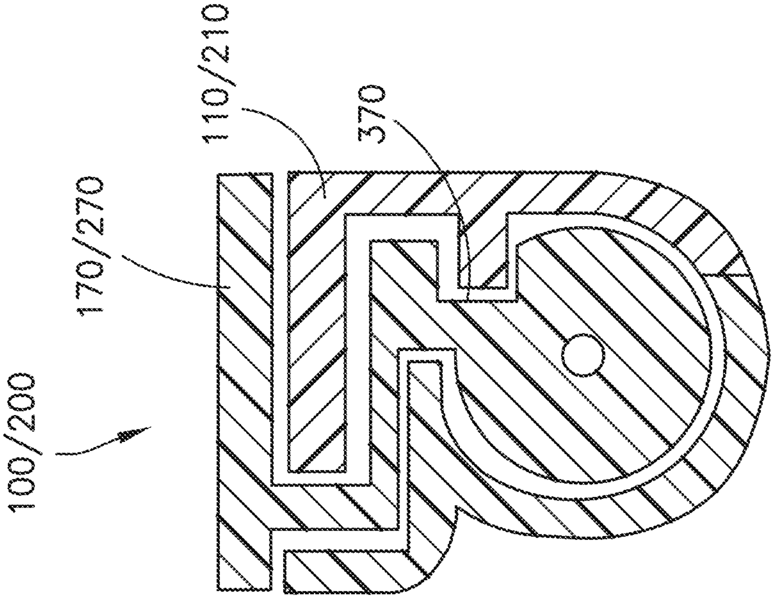
FIG. 17 is a cross-sectional view of a blood draw device in accordance with a further aspect of the present disclosure.
Figure 18:
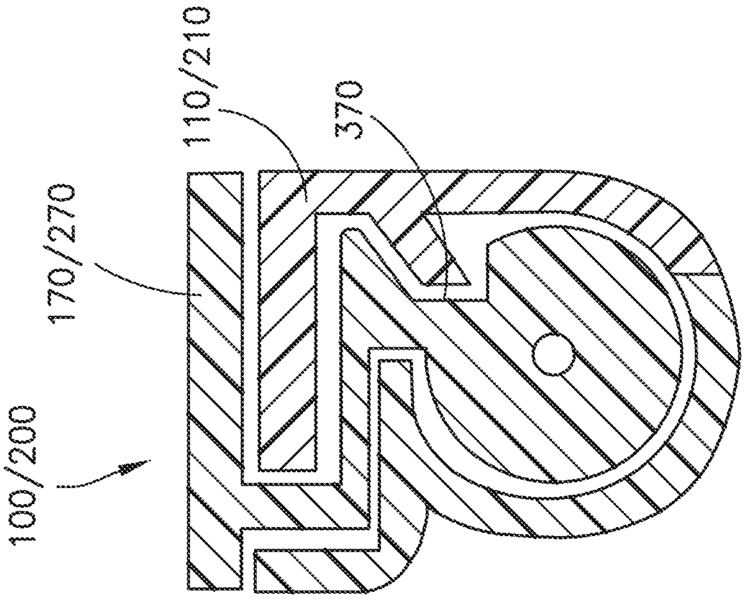
FIG. 18 is a cross-sectional view of a blood draw device in accordance with a further aspect of the present disclosure.
Figure 19:
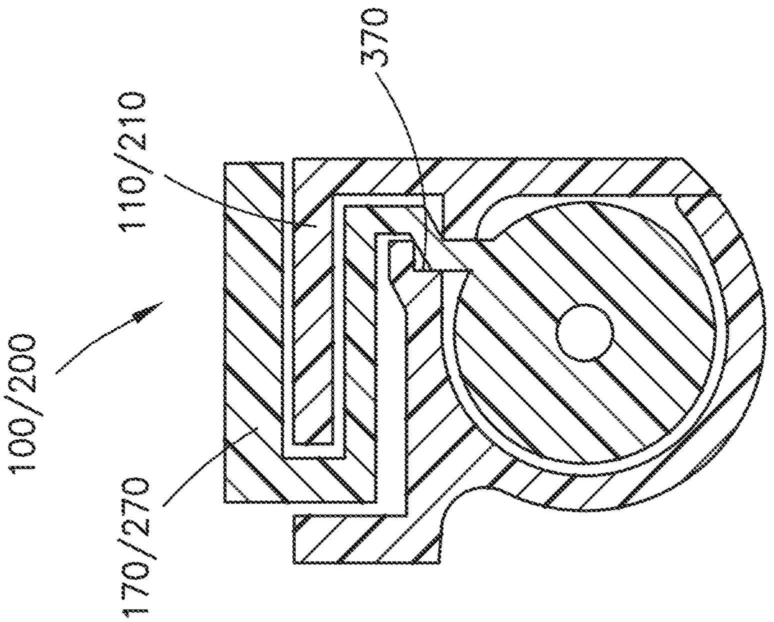
FIG. 19 is a cross-sectional view of a blood draw device in accordance with a further aspect of the present disclosure.

Referring to FIGS. 17-19, in further aspects or embodiments of the present application, the introducer 110, 210 of either of device 100 or device 200, may be similar to the embodiments of FIGS. 11 and 12, but include various geometries of the actuator 170, 270 and a gap 370 between the first portion 114, 214 and the second portion 115, 215 of the introducer 110, 210. The gap 370 and/or the portion of the actuator 170, 270 extending through the gap 362 may define a tortuous path and include various confined spaces configured to prevent the catheter 160, 260 from passing through the gap 370.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A blood draw device for use with a peripheral intravenous catheter (PIVC) comprising:

a catheter having a proximal end, a distal end, and a sidewall therebetween defining a lumen;

an introducer having a proximal end, a distal end, and a sidewall therebetween defining an inner volume configured to movably receive the catheter, the introducer having a top surface and a bottom surface positioned opposite to the top surface; and an actuator movably coupled to the introducer, the actuator is configured to move relative to the introducer to move the catheter between a first position, in which the distal end of the catheter is disposed within the introducer, and a second position, in which the distal end of the catheter is disposed beyond the distal end of the introducer, wherein the introducer comprises a first portion and a second portion with a ridge positioned within the inner volume and extending radially inward, the ridge being positioned on a vertical sidewall of the second portion of the introducer or the ridge being positioned on a horizontal wall of the second portion of the introducer, the ridge extending in a direction extending from the proximal end of the introducer to the distal end of the introducer, the ridge is configured to engage a portion of the catheter during use of the blood draw device.

2. The blood draw device of claim 1, wherein the ridge extends from the distal end of the introducer to the proximal end of the introducer.

3. The blood draw device of claim 1, wherein the ridge extends only a portion of a length extending from the distal end of the introducer to the proximal end of the introducer.

4. The blood draw device of claim 1, wherein the ridge is positioned closer to the top surface than the bottom surface of the introducer.

5. The blood draw device of claim 4, wherein the second portion is attached to the first portion, and wherein the horizontal wall defines at least a portion of the top surface of the introducer.

6. A blood draw device for use with a peripheral intravenous catheter (PIVC) comprising:

a catheter having a proximal end, a distal end, and a sidewall therebetween defining a lumen;

an introducer having a proximal end, a distal end, and a sidewall therebetween defining an inner volume configured to movably receive the catheter, the introducer comprising an actuator surface defining an actuator space, the introducer having a top surface and a bottom surface positioned below the top surface;

an actuator movably coupled to the introducer, the actuator is configured to move relative to the introducer to move the catheter between a first position, in which the distal end of the catheter is disposed within the introducer, and a second position, in which the distal end of the catheter is disposed beyond the distal end of the introducer, the actuator having a first portion disposed outside of the introducer and a second portion disposed in the inner volume of the introducer, the second portion of the actuator comprising a lower body positioned within the actuator space; and a rail insert having an outer top surface in contact with the actuator surface and an outer bottom surface, the rail insert positioned between the lower body of the second portion of the actuator and the actuator surface, the rail insert extending in a direction extending from the proximal end of the introducer to the distal end of the introducer, the outer bottom surface of the rail insert is configured to engage a portion of the catheter during use of the blood draw device.

7. The blood draw device of claim 6, wherein the actuator moves relative to the rail insert.

8. The blood draw device of claim 6, wherein the rail insert is flexible.

9. The blood draw device of claim 6, wherein the rail insert extends only a portion of a length extending from the distal end of the introducer to the proximal end of the introducer.

* * * * *